(12) United States Patent
Van Bladel et al.

(10) Patent No.: US 7,311,672 B2
(45) Date of Patent: *Dec. 25, 2007

(54) DEVICE FOR BIOPSY OF TUMORS

(75) Inventors: Kevin H. Van Bladel, Pleasanton, CA (US); Shigeru Tanaka, Halfmoon Bay, CA (US); Daren L. Stewart, Pleasanton, CA (US)

(73) Assignee: Sanarus Medical, Inc., Pleasanton, CA (US)

( * ) Notice: Subject to any disclaimer, the term of this patent is extended or adjusted under 35 U.S.C. 154(b) by 564 days.

This patent is subject to a terminal disclaimer.

(21) Appl. No.: 10/421,598

(22) Filed: Apr. 22, 2003

(65) Prior Publication Data

US 2003/0195436 A1  Oct. 16, 2003

Related U.S. Application Data

(63) Continuation of application No. 09/847,931, filed on May 3, 2001, now Pat. No. 6,551,255, which is a continuation-in-part of application No. 09/690,321, filed on Oct. 16, 2000, now Pat. No. 6,540,694.

(51) Int. Cl.
*A61B 10/00* (2006.01)
(52) U.S. Cl. ..................................... 600/564
(58) Field of Classification Search ........ 600/562–568; 606/21, 23, 28, 29, 184; 604/164.01; 219/229, 219/230; 62/293; 83/171; 30/140; 128/898; 418/88, 95, 256
See application file for complete search history.

(56) References Cited

U.S. PATENT DOCUMENTS 3,360,192 A * 12/1967 Van Hees ..................... 418/88
3,391,690 A * 7/1968 Armao ......................... 600/564
3,598,108 A * 8/1971 Jamshidi et al. ............. 600/567
4,644,951 A    2/1987 Bays ........................... 128/305

(Continued)

FOREIGN PATENT DOCUMENTS

DE         19806693 A1    8/1999

(Continued)

OTHER PUBLICATIONS

Tyco Minimally Invasive Breast Biopsy.

(Continued)

*Primary Examiner*—Max F. Hindenburg
*Assistant Examiner*—Brian Szmal
(74) *Attorney, Agent, or Firm*—K. David Crockett, Esq.; Crockett & Crockett

(57) ABSTRACT

A device and method of use for securing and coring of tumors within the body during a biopsy of the tumor, specifically breast tumors. An adhesion probe for securing the tumor is described. The probe secures the tumor by piercing the tumor and providing a coolant to the distal tip to cool the tip. The cooled tip adheres to the tumor. A coring instrument adapted for cutting a core sample of the tumor is described. The instrument is provided with a cannula that can cut a core sample of the tumor. The instrument is adapted for use with the probe with the probe fitting within the cannula. The instrument can be used in conjunction with the probe to secure and core a sample of the tumor for biopsy.

27 Claims, 12 Drawing Sheets

U.S. PATENT DOCUMENTS

| | | | |
|---|---|---|---|
| 5,027,827 A | 7/1991 | Cody et al. | 128/753 |
| 5,056,523 A | 10/1991 | Hotchkiss, Jr. et al. | 128/653 |
| 5,056,532 A | 10/1991 | Hull et al. | 128/785 |
| 5,133,360 A | 7/1992 | Spears | 128/754 |
| 5,234,000 A | 8/1993 | Hakky et al. | 600/564 |
| 5,353,804 A | 10/1994 | Kornberg et al. | 128/754 |
| 5,649,547 A | 7/1997 | Ritchart et al. | 128/754 |
| 5,769,086 A | 6/1998 | Ritchart et al. | 128/753 |
| 5,775,333 A | 7/1998 | Burbank et al. | 600/567 |
| 5,810,806 A | 9/1998 | Ritchart et al. | 604/21 |
| 5,833,685 A | 11/1998 | Tortal et al. | 606/23 |
| 5,868,673 A | 2/1999 | Vesely | 600/407 |
| 5,913,857 A | 6/1999 | Ritchart et al. | 606/45 |
| 5,928,164 A | 7/1999 | Burbank et al. | 600/567 |
| 5,944,673 A | 8/1999 | Gregoire et al. | 600/564 |
| 5,964,716 A | 10/1999 | Gregoire et al. | 600/564 |
| 6,007,497 A | 12/1999 | Huitema | 600/567 |
| 6,017,316 A | 1/2000 | Ritchart et al. | 600/567 |
| 6,050,955 A | 4/2000 | Bryan et al. | |
| 6,238,355 B1 | 5/2001 | Daum | |
| 6,273,862 B1 | 8/2001 | Privitera et al. | |
| 6,277,083 B1 | 8/2001 | Eggers et al. | 600/564 |
| 6,378,525 B1 * | 4/2002 | Beyar et al. | 128/898 |
| 6,540,694 B1 * | 4/2003 | Van Bladel et al. | 600/564 |
| 6,551,255 B2 * | 4/2003 | Van Bladel et al. | 600/584 |
| 6,712,773 B1 * | 3/2004 | Viola | 600/564 |

FOREIGN PATENT DOCUMENTS

| | | | |
|---|---|---|---|
| JP | 2000152941 A | 6/2000 | |
| WO | WO 97/20504 | 6/1997 | |
| WO | WO9525465 A | 6/1997 | |
| WO | WO 98/06346 | 2/1998 | |
| WO | WO 98/08441 | 3/1998 | |
| WO | WO9913775 A | 3/1999 | |
| WO | WO 99/44506 | 9/1999 | |
| WO | WO 00/12009 | 3/2000 | |

OTHER PUBLICATIONS

Breast Care Info Web Page: Steps in the Mammotome Procedure.
Open Excisional Surgical Biopsy: Breast Biopsy Website.
Stereotactics in Breast Biopsy: Breast Biopsy Website.
G.S. Ferzli et al., *Advanced Breast Biopsy Instrumentation: A Critique*, Journal of American College of Surgeons; 1997; 185:145-151.
Edgar D. Staren, MD et al., *Ultrasound-Guided Needle Biopsy of the Breast*, Surgery; Oct. 1999, 629-625.
Parker et al., *Performing a Breast Biopsy with a Directional, Vacuum-Assisted Biopsy Instrument*, Radiographics; Sep.-Oct. 1997; 17(5):1233-52.
Jackman RJ et al., *Needle-Localized Breast Biopsy: Why Do We Fail48* , Radiology Sep. 1997, 204(3); 677-84.
Jackman RK et al., *Percutaneous Removal of Benign Mammographic Lesions: Comparison of Automated Large-Core and Directional Vacuum-Assisted Stereotactic Biopsy Techniques*, AJR Am J Roentgenol Nov. 1998; 171(5), 1325-30.
Biopsy Mammotome Brochure.
Bard Product Brochure.

* cited by examiner

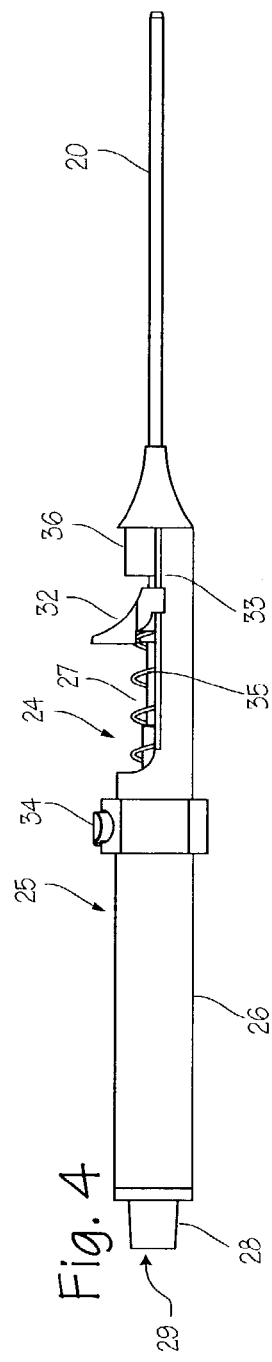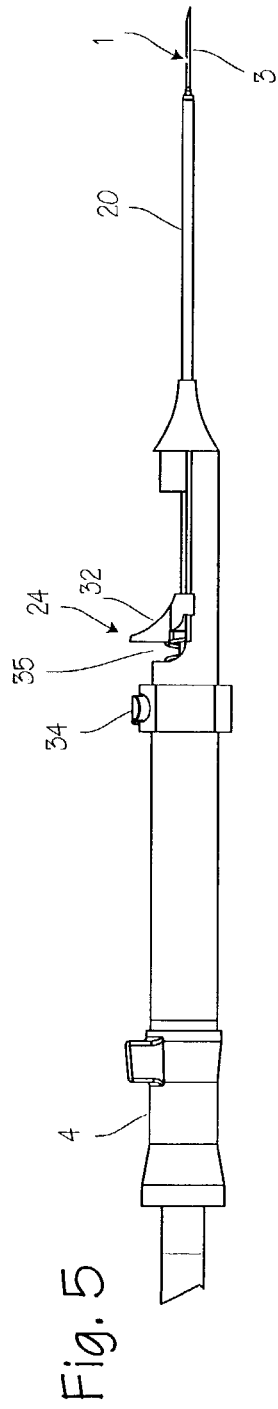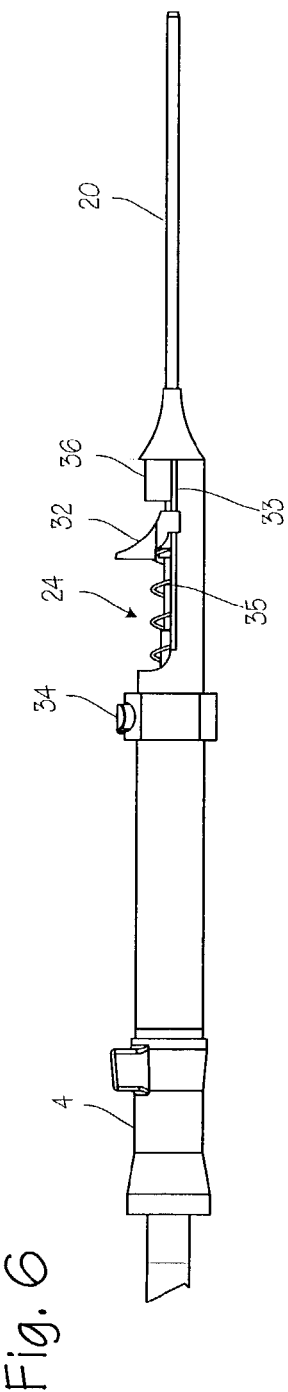

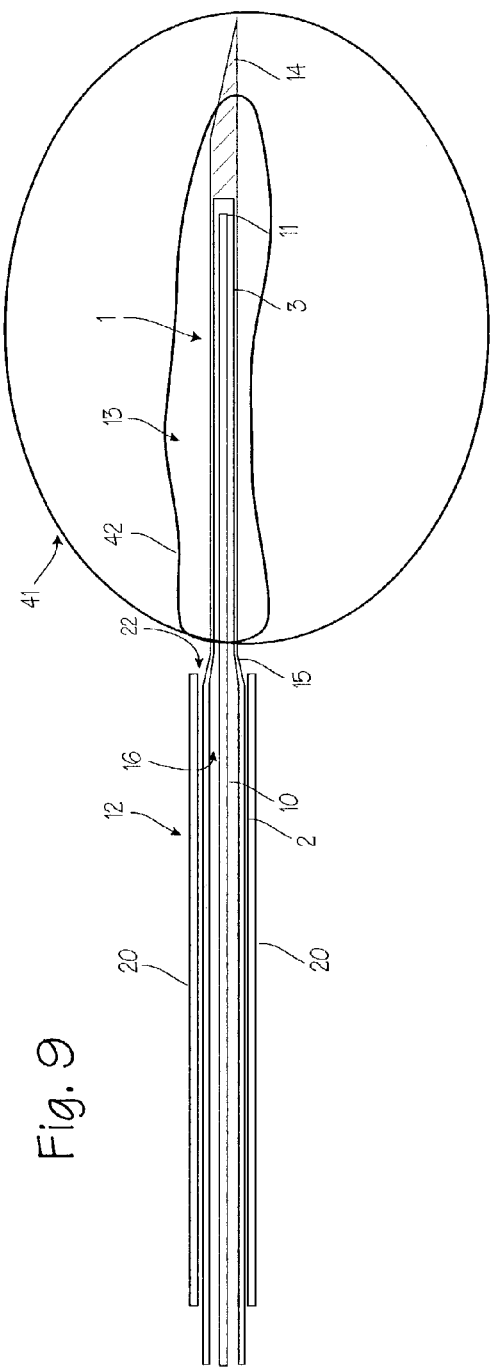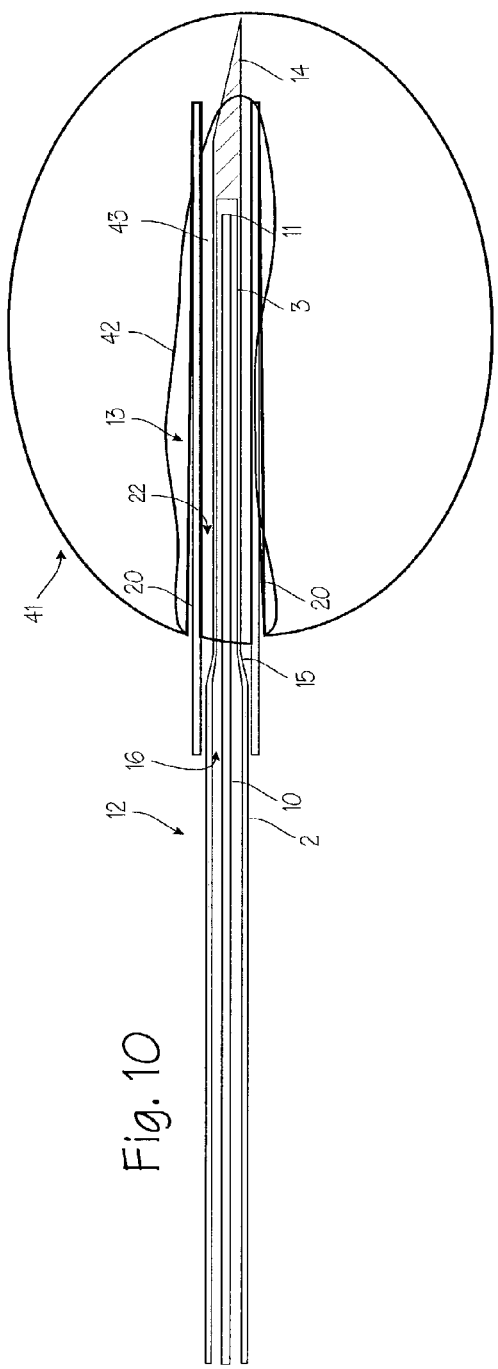

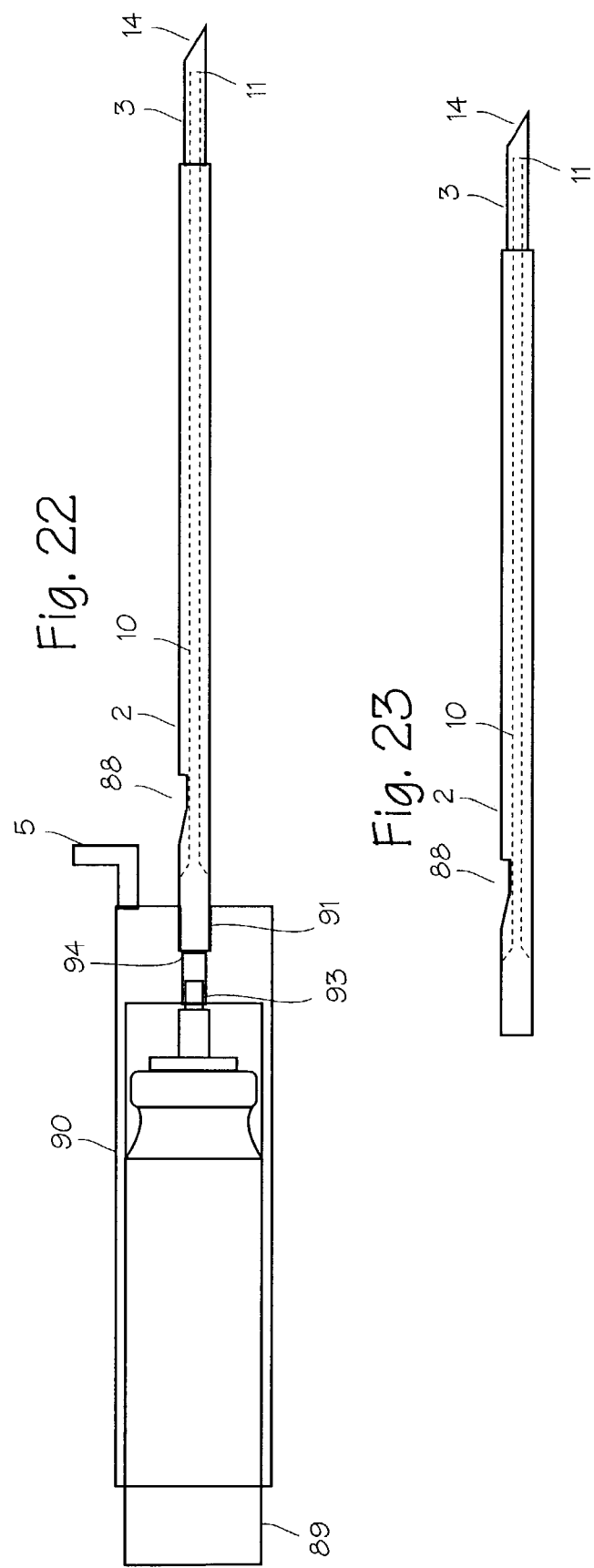

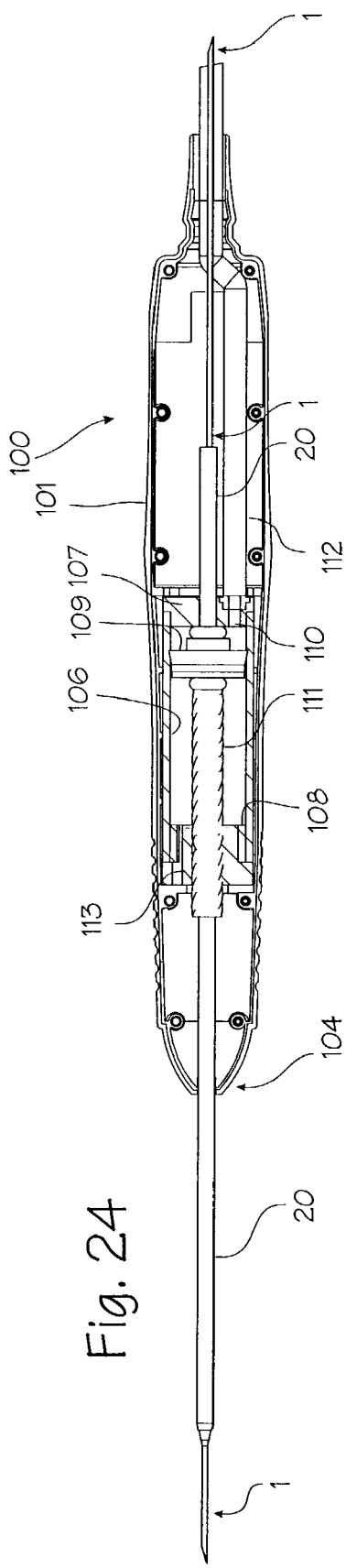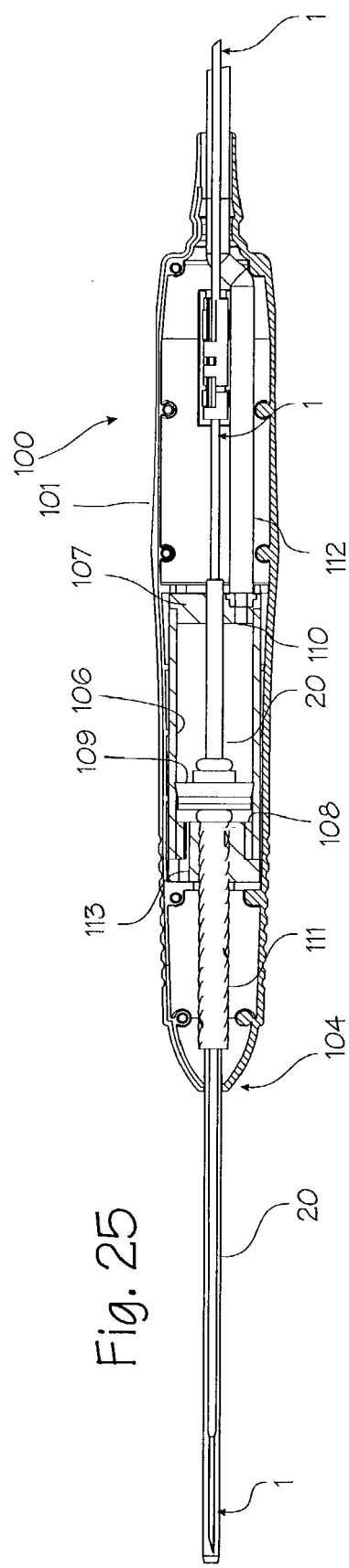

DEVICE FOR BIOPSY OF TUMORS

This application is a continuation application of U.S. application Ser. No. 09/847,931, filed May 3, 2001, now U.S. Pat. No. 6,551,255, which is a continuation-in-part application of U.S. application Ser. No. 09/690,321, filed Oct. 16, 2000, now U.S. Pat. No. 6,540,694.

FIELD OF THE INVENTIONS

The devices and method described below relate to the diagnosis and treatment of breast lesions, and more generally, to the diagnosis and treatment of tumors and lesions throughout the body.

BACKGROUND OF THE INVENTIONS

Biopsy is an important procedure used for the diagnosis of patients with cancerous tumors, pre-malignant conditions, and other diseases and disorders. Typically, in the case of cancer, when the physician establishes by means of procedures such as palpation, mammography or x-ray, or ultrasound imaging that suspicious circumstances exist, a biopsy is performed. The biopsy will help determine whether the cells are cancerous, the type of cancer, and what treatment should be used to treat the cancer. Biopsy may be done by an open or percutaneous technique. Open biopsy, which is an invasive surgical procedure using a scalpel and involving direct vision of the target area, removes the entire mass (excisional biopsy) or a part of the mass (incisional biopsy). Percutaneous biopsy, on the other hand, is usually done with a needle-like instrument through a relatively small incision, blindly or with the aid of an imaging device, and may be either a fine needle aspiration (FNA) or a core biopsy. In FNA biopsy, individual cells or clusters of cells are obtained for cytologic examination and may be prepared such as in a Papanicolaou smear. In core biopsy, as the term suggests, a core or fragment of tissue is obtained for histologic examination which may be done via a frozen section or paraffin section. One important area where biopsies are performed is the diagnosis of breast tumors.

Traditionally, the biopsy technique for breast tumors involves placing a biopsy device multiple times into the breast and taking several samples of tissue from a mass or tumor which is suspected of being cancerous. Several samples are required to be sure that some tissue from the suspect mass has been captured, and enough tissue has been sampled to ensure that, if disperse cancer cells exist in the suspect mass some of those cancer cells will be captured in the samples. Each time the device is placed the physician must locate and direct the device with ultrasound imaging into the correct position near the suspect mass. Some breast tumors and lesions are very well defined, hard spherical masses which grow within the soft, compliant breast tissue. It is difficult to force a needle into these lesions because they are resistant to puncture and fairly mobile. Forcing the biopsy needle into the lesion is like trying to spear an apple floating in water.

Vacuum assisted biopsy system proposed by Biopsys involves sucking a breast lesion into a cannula and shearing off the captured edge of the lesion to obtain a biopsy sample. The device uses a vacuum to collect tissue into the side of an open tubular device, and then uses a rotating corer to cut the tissue collected. The rotating corer is slidable within the tubular section and can be pulled back to remove the tissue collected in the rotating corer. An additional stylet inside the rotating corer can be used to push the tissue out of the corer. The device can be rotated on its axis to remove a sample, 360 degrees around the central placement of the device. Typically, physicians sample six to eight cores. One advantage of this device is that the physician does not have to remove the device for additional biopsy samples. However, the tumor itself must be re-engaged after every coring operation, which entails substantial effort in relocation and confirmation that the target suspect mass has been engaged by the side aperture. Tumors may be too tough to yield to the suction and deform as necessary to enter the side opening of the cannula. Doctors also currently use the device to take a circular sequence of cores by rotating the device about its long axis or by sideways movement of the suction head to take a line of cores.

After biopsy and analysis, the tumor must be treated with a separate device, as Biopsys teaches that their coring device should not be used for resection. Indeed, the device is not designed to perform resection with assurance that complete resection of a suspect mass has been accomplished. Mechanical cutting and disruption of the tissue structure and cancer cell dispersion (that is, tearing of the tissue around the cancer and movement of the cancer cells amongst normal tissue) will result in unintentional delivery of cancer cells into healthy tissue adjacent the lesion.

SUMMARY

The devices and methods described below provide for diagnosis of tumors within the breast. The devices include a probe with structures that permit the surgeon to secure a suspect mass or tumor within the breast during the biopsy procedure. The probe is provided with a rigid tube and a sharp distal tip. To secure the tumor to the probe, the surgeon pierces the tumor with the distal rod. Gas tubing extending within the rigid tube directs coolant to the distal tip to cool the tip, the tumor then adhering to the cooled probe.

The devices also include a coring apparatus with structures that permit the surgeon to core a sample of the tumor during the biopsy procedure. The coring apparatus is provided with a cannula that advances through a tumor to core a sample of the tumor. The coring apparatus is adapted for use with the probe. The probe is inserted into the cannula with the distal tip of the probe extending beyond the distal tip of the cannula. The surgeon can insert the devices into the body until the probe pierces the tumor. Coolant is directed to the distal tip of the probe to lightly cool the distal tip and the tumor. The lightly cooled distal tip adheres to the tumor cells. Once secured to the probe, the surgeon can core a sample of the tumor with the coring apparatus. After coring is complete, the surgeon can retract the device with the core sample. This method of biopsy prevents destruction of the tumor cells and reduces the dispersion of tumor cells to healthy cell areas.

BRIEF DESCRIPTION OF THE DRAWINGS

FIG. 4 illustrates the biopsy instrument adapted for use with the adhesion probe of FIGS. 1 and 2.

FIGS. 5 and 6 illustrate the biopsy instrument adapted with the adhesion probe of FIGS. 1 and 2.

FIG. 9 illustrates a method of breast tumor biopsy using the device of FIGS. 5 and 6.

FIG. 10 illustrates a method of breast tumor biopsy using the device of FIGS. 5 and 6.

FIGS. 22 and 23 illustrate an embodiment of the adhesion probe which uses a coolant supplied in small bottles.

FIGS. 24 and 25 show a cross-sectional view of a pneumatically operated biopsy instrument, with the adhesion probe of FIG. 1 in place within the biopsy instrument.

DETAILED DESCRIPTION OF THE INVENTIONS

Figure 1:
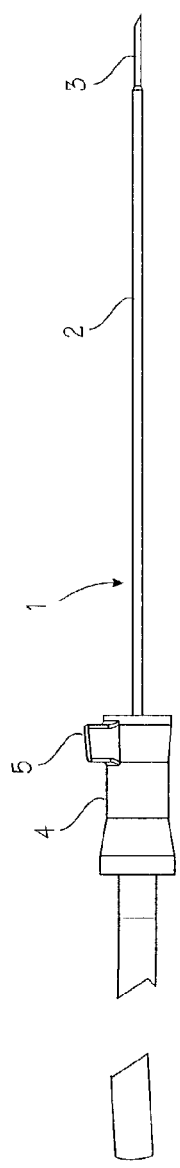
FIG. 1 illustrates the adhesion probe for securing a breast tumor during a biopsy or ablation procedure.

FIG. 1 illustrates an adhesion probe 1 for securing a breast tumor during a biopsy or resection procedure. This probe uses Joule-Thomson cooling or liquid nitrogen to create a lightly cooled region at the distal tip. This lightly cooled region adheres to a suspect lesion or tumor. The adhesion probe 1 comprises a long, slender yet rigid tube 2. A short rigid penetrating segment 3 extends distally from the distal end of the rigid tube, and a suitable handle 4 is mounted on the proximal end of the tube. The handle includes a quick release mechanism which is operable through quick release actuator 5.

Figure 2:
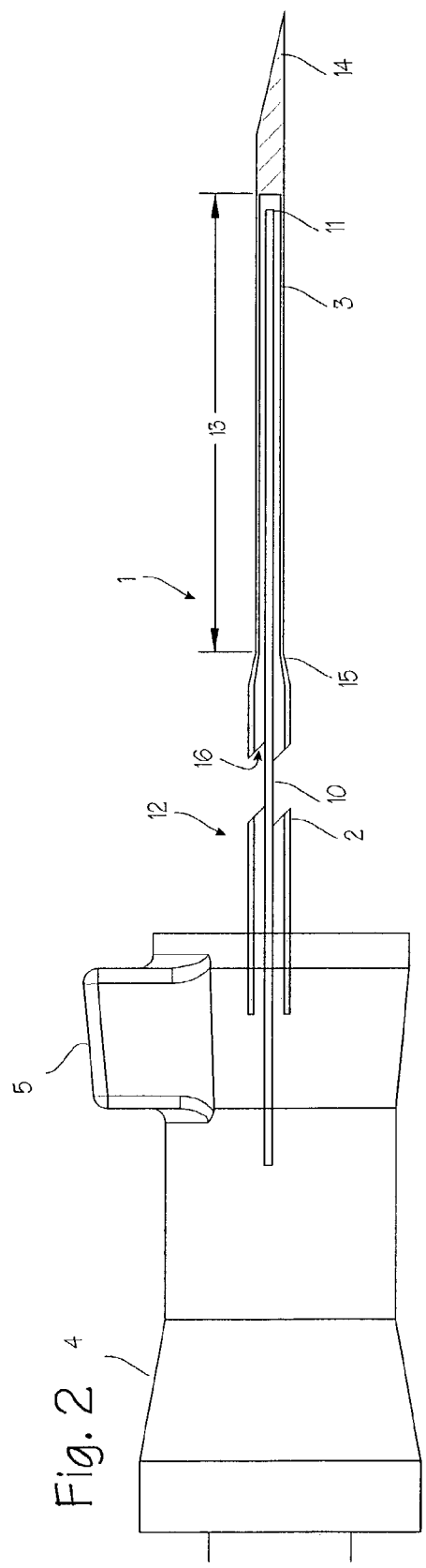
FIG. 2 is a cross section of the adhesion probe of FIG. 1.

FIG. 2 illustrates the adhesion probe 1 in cross section, showing the rigid tube 2, the distal penetrating segment 3 and the handle 4. A coolant inlet tube 10 passes through the handle and the rigid tube, extending to the distal end of the rigid tube, and terminating just proximal of the distal tip of the penetrating segment. The inlet tube has an orifice 11 at the distal end of the inlet tube, which may be merely a straight cut termination of the tube or a small nozzle of smaller internal diameter than the immediately upstream portion of the inlet tube. The rigid tube has a proximal segment 12 having an outer diameter of about (0.065) inches, an internal diameter of about (0.047) inches, and a length of about (10) inches. The penetrating segment 3 comprises a first segment 13 and a sharp distal tip 14. The first segment has an outer diameter of about (0.043) inches, an inner diameter of about (0.033) inches, and a length of about (1) inch. As can be seen from the cross section, the sharp distal tip is solid and adapted for piercing through a tumor. The length of the penetrating segment is chosen to be approximately the same size as the target tissue mass to be sampled, or the size of the desired core sample. This penetrating segment is forced into a lesion or tumor.

Between the proximal segment of the rigid tube and the first segment of the penetrating segment is a tapered segment 15 of the rigid tube of about (0.05) inches long where the inner and outer diameters of the rigid tube tapers from the diameters of the proximal segment to the diameters of the first segment. An annular cavity or lumen 16 is created by the outer surface of the inlet tube and the inner surface of the rigid tube. The gas and/or liquid exiting the orifice of the inlet tube counterflows along the annular cavity and is exhausted from the probe to a suitable point far removed from the probe. If gas such as Argon is chosen, the gas undergoes a Joule Thompson expansion as the gas is directed out through the orifice. As the gas and/or liquid are directed to the penetrating segment and out through the orifice, the surface area about the penetrating segment is cooled. Cooling with argon gas supplied to the probe with the dimensions described above at a pressure of about 1200-2000 psi will provide cooling to a temperature range of about 0° C. to −10° C. With gas supplied at 3000 psi, the adhesion probe will attain a low temperature of about −60° C. in water. The gas or liquid used for cooling may include gaseous argon, nitrogen, carbon dioxide, air, liquid nitrogen, freon, CFC's. perflourocarbons, or any other suitable coolant. Gas may be provided through a cryosurgical system such as Endocare's Cryocare® cryosurgical systems.

Figure 3:
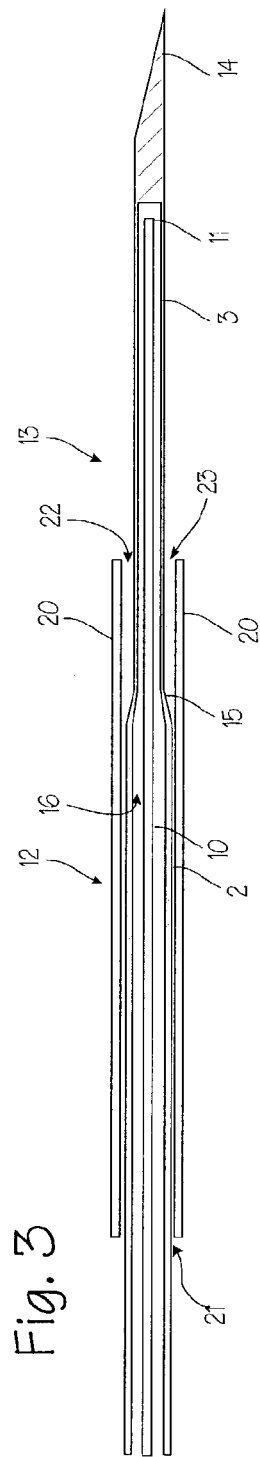
FIG. 3 illustrates the adhesion probe within a coring cannula.

FIG. 3 illustrates the rudimentary relationship between the coring cannula 20 and the adhesion probe 1. The cannula is a slender yet rigid tube having a proximal opening 21 and a distal opening 22, and a lumen 23 extending through the cannula from the proximal end of the cannula to the distal end. The cannula is slidably disposed around the adhesion probe, and may be longitudinally translated relative to the adhesion probe. The cannula is adapted for insertion through a small incision in the skin, and may be inserted along with the adhesion probe or over the adhesion probe. As described in the following figures, the cannula may be forced distally over the penetrating segment to core any tissue which is secured to the penetrating segment from any surrounding body tissue.

FIG. 4 illustrates a spring-loaded biopsy instrument 24 adapted for use with the adhesion probe 1 and the cannula 20. The biopsy instrument comprises a housing 25. The housing comprises a grip 26, sized for a human hand, and a receptacle 27 distal to the grip. At the proximal end of the housing, a fitting 28 with an inlet 29 communicates with the lumen of the cannula. The cannula extends from within the housing at the inlet and out through the distal end of the housing.

The biopsy instrument 24 includes a coring mechanism. The coring mechanism comprises a cannula translating mechanism housed within the receptacle 27. A block 32 is slidably mounted on rails 33 attached to or integrally formed to the housing 25. A trigger button 34 capable of coupling with the block is preferably positioned about the grip 26 for ease of operation of the button by the same hand holding the grip. A spring 35 is interposed between the block and the trigger button. The spring exerts a distally urging force to the block. At the distal end of the receptacle is a stopper 36 attached to or integrally formed into the housing. The cannula 20 is fixedly fitted through the block and urged distally forward by the spring. The distally urging force of the spring forces the block and therefore the cannula to distally translate. The spring may have a spring constant between 5 to 15 lbs. per inch, and is preferably between 7 and 11 lbs. per inch.

FIGS. 5 and 6 show the adhesion probe 1 in place within the lumen 23 of the cannula 20. The adhesion probe can be inserted into and through the lumen from the proximal opening 21 of the cannula. To secure the probe to the biopsy instrument 24, the handle 4 of the probe is fitted to the fitting 28. The gas and/or liquid source is connected to the handle via the feed line.

The cannula translating mechanism has a locked position and an unlocked position. FIG. 5 illustrates the translating mechanism in the locked position. In the locked position, the spring 35 is compressed and the block 32 is coupled to the trigger button 34. The penetrating segment 3 of the adhesion probe is exposed, extending distally from the cannula 20. FIG. 6 illustrates the translating mechanism in the unlocked position, with the cannula translated distally over the penetrating segment. To move the translating mechanism from the locked position to the unlocked position, the trigger button is depressed. As the button is depressed, the block uncouples from the button and the urging force from the compressed spring urges the block and the cannula distally forward. (Any suitable latching mechanism may be used to releasably secure the block in the proximal position and release the block as desired by the operator of the device.) As the block is urged distally forward, the block and the cannula translate along the rails 33 until the block engages the stopper 36. As the cannula translates distally over the penetrating segment of the adhesion probe, any tissue stuck to the penetrating segment is cored from the surrounding lesion, and may be removed with the device.

FIGS. 7 through 10 illustrate the device in use. At the start of the biopsy procedure, the patient is prepared and the breast is appropriately prepped and draped. The site is prepared using local anesthesia and optionally, intravenous sedation. The patient is positioned on the operating table in the supine position, with the patient on her back. (If the procedure is accomplished under stereotactic guidance, the patient may be prone on a stereotactic table, exposing the breast below the table.) The breast is imaged, if not previously imaged, to determine the location of the tumors. A small incision of about (4) mm is made in the breast to allow the adhesion probe 1 and cannula 20 to be easily inserted into the skin. The adhesion probe is inserted into the biopsy instrument 24 so that it is positioned within the cannula, the penetrating tip 3 extending distally from the distal end of the cannula 20. The cannula translating mechanism is set in the locked position, leaving the penetrating segment outside the cannula. The distal end of the device, including the penetrating segment of the adhesion probe and the distal end of the cannula, is inserted into the breast through the incision. The distal end of the device is maneuvered to the target lesion within the breast under stereotactic or ultrasound guidance.

Figure 7:
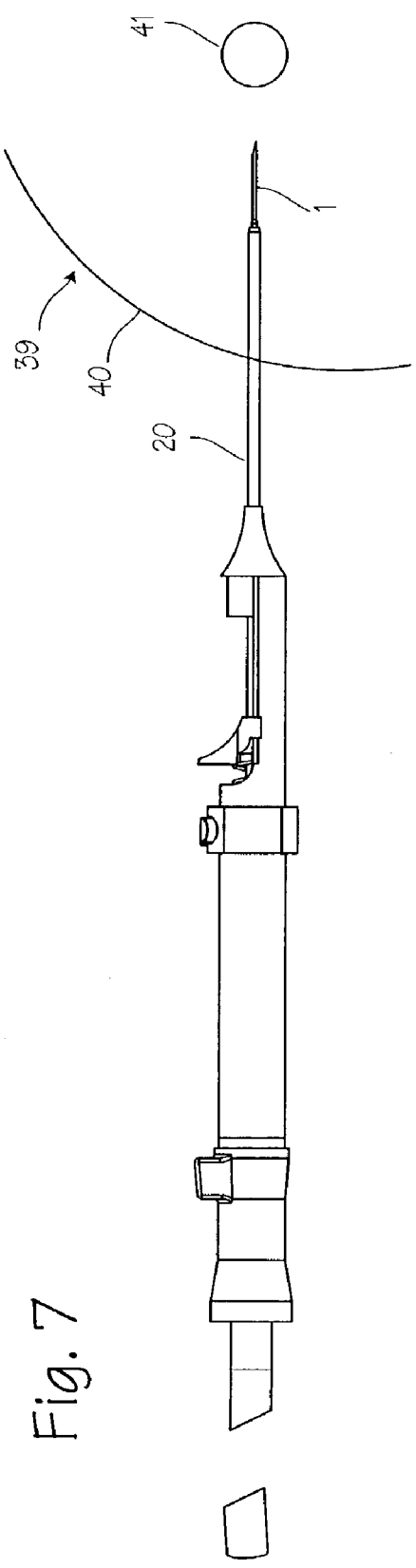
FIG. 7 illustrates a method of breast tumor biopsy using the device of FIGS. 5 and 6.

The coring procedure is illustrated in FIGS. 7 through 10. FIG. 7 shows the adhesion probe 1 and the cannula 20 being inserted through the incision made in the skin overlying the tumor. The adhesion probe has been inserted into the cannula so that it is coaxially disposed within the cannula, and its distal penetrating segment protrudes from the distal end of the cannula. The handle has been secured to the proximal end of the instrument 24, so that the adhesion probe and biopsy instrument are latched together via the quick release mechanism. The adhesion probe and biopsy instrument can thus be manipulated as a single piece. The patient's breast 39 and skin 40 are shown schematically. The tumor, lesion or other suspect mass 41 is located within the breast, surrounded by soft tissue and fatty tissue. An ultrasound scanner or other imaging device is used to obtain an image of the breast, including the tumor and any device inserted into the breast, and the surgeon uses the display from the imaging device to assist in guidance of the probe and the cannula to the tumor.

Figure 8:
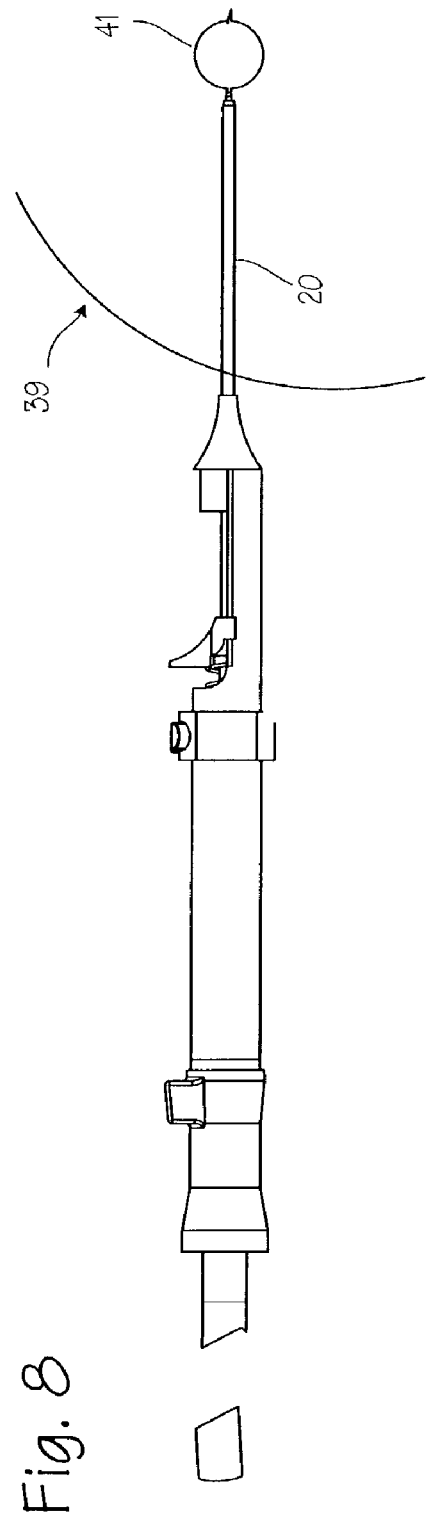
FIG. 8 illustrates a method of breast tumor biopsy using the device of FIGS. 5 and 6.

FIG. 8 illustrates the adhesion probe 1 and the cannula 20 being inserted into the breast 39 until the probe penetrates the tumor 41. The surgeon pushes the probe and the cannula into the breast until the penetrating segment 3 of the adhesion probe pierces through the tumor and until the tapered segment 15 of the rigid tube 2 is proximate to the tumor.

FIG. 9 illustrates the adhesion probe 1 being activated to secure the tumor 41. To secure the tumor to the probe during the biopsy procedure, the surface area about the penetrating segment 3 is cooled. Either gas or liquid is directed from the source to the penetrating segment. If the surgeon uses gas, as the gas is directed out through the orifice 11 of the coolant inlet tube 10, the gas undergoes a Joule-Thomson effect to freeze the surface area about the penetrating segment. The gas source can be a high compression tank or a whippet. The surface area is frozen to a temperature range of about 0° C. to −60° C. At this temperature range, the cooled surface area does not ablate the tumor cells to hinder tumor cell analysis. Only a relatively small amount of gas or liquid is needed to cool the surface area to this temperature range. The gas or liquid exiting the orifice and counterflowing along the annular cavity 16 is exhausted from the probe. The cooled surface area freezes a thin layer of tumor cells in contact about the cooled surface area, and the tumor is secured to the probe. The cooled annular volume of body tissue is illustrated in FIG. 9 as item 42.

FIG. 10 illustrates activation of the cannula translating mechanism to cut a core sample of the frozen tumor 41. Once the tumor is secured to the probe 1, the biopsy instrument 24 is activated to core a sample of the frozen tumor. To begin coring the tumor, the translating mechanism is operated via the trigger button 34 (see FIG. 5). The trigger button is depressed and the cannula 20 advances distally towards the frozen tumor. As the cannula contacts the tumor and advances towards the sharp distal tip, the cannula cuts a sample 43 of the frozen tumor. The resulting core sample is a layer of frozen or partially frozen tumor tissue about the penetrating segment 3. Because the tumor is frozen, dispersion and seeding of the tumor cells to healthy areas of the breast is minimized compared to normal biopsy methods.

Figure 11:
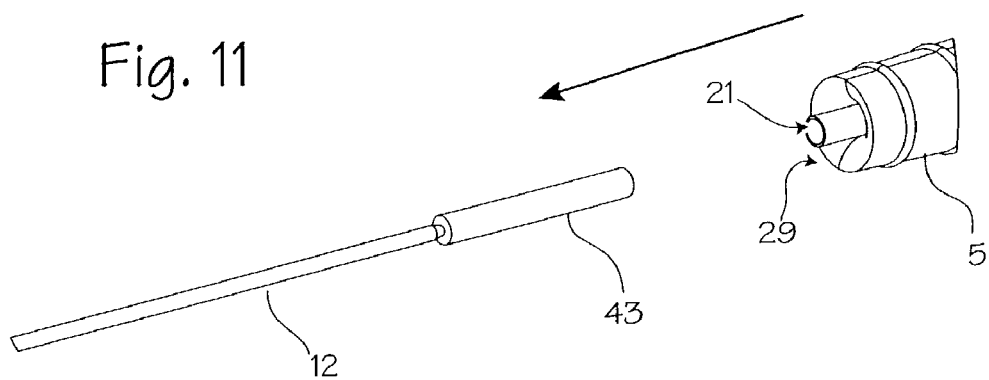
FIG. 11 illustrates the adhesion probe withdrawn from the biopsy instrument.
Figure 12:
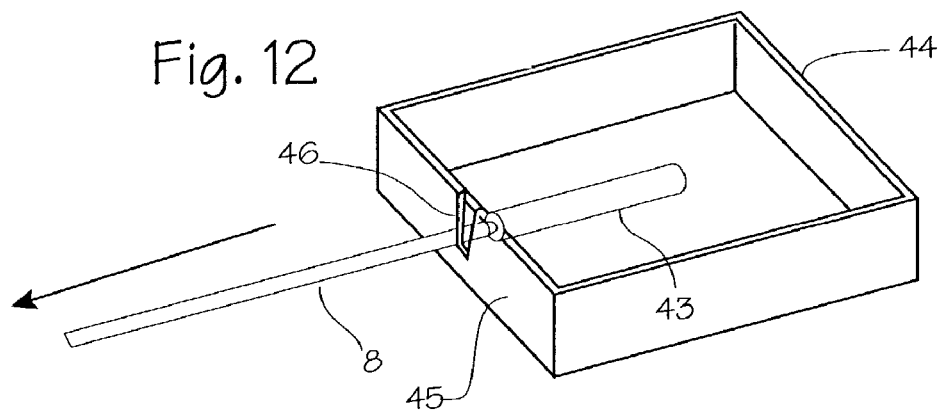
FIG. 12 illustrates the holding tray for holding the adhesion probe.

Once a sample of the breast tumor 41 is cored, the adhesion probe 1 with the secured core sample remains within the cannula 20. To remove the core sample from the breast 39, the biopsy instrument 24 and the adhesion probe are retracted from the breast, with the core sample still protected within the cannula during retraction. Once the biopsy instrument and probe are retracted outside the breast, the adhesion probe with the core sample 43 is withdrawn from the biopsy instrument out from the inlet 29, or out the proximal opening 21 of the cannula, as shown in FIG. 11. The sample is still secured to the penetrating segment of the adhesion probe 1. The sample thaws in a short time, and can be moved to a holding tray shown in FIG. 12. The holding tray 44 has a wall 45 which has one or more slots 46. For at least a portion of the slot height, the width of the slots approximates the outer diameter of the penetrating segment of the adhesion probe, so that the adhesion probe may be slipped down into the groove and pulled out horizontally, allowing the sample to be cleanly scraped off of the penetrating segment. The adhesion probe and holding tray may be provided as disposables in a kit sold for each procedure performed by a physician.

Another method of using the system facilitates multiple sampling during a single placement of the biopsy instrument 24. After placement of the biopsy instrument and adhesion probe 1, adhesion of the adhesion probe to the tumor 41 and translation of the cannula 20 over the penetrating segment 3, the adhesion probe may be pulled proximally out of the cannula while leaving the cannula and biopsy instrument in place in the breast 39. The tissue which adheres to the adhesion probe is then removed. Leaving the cannula in the advanced position within the patient's breast, the adhesion probe may then be re-inserted into the cannula (in the same space or biopsy track). The cannula is then pulled back, exposing the penetrating segment within the tumor (and within the initial cored space). While light pressure is applied around the breast, the adhesion probe is cooled, freezing an additional cylindrical volume of tissue surrounding the probe. The cannula may then be advanced to core out the frozen volume of tissue. Successive cylindrical core samples are thereby obtained. In our own studies, this procedure yielded seventeen successive cylindrical core samples.

Figure 13:
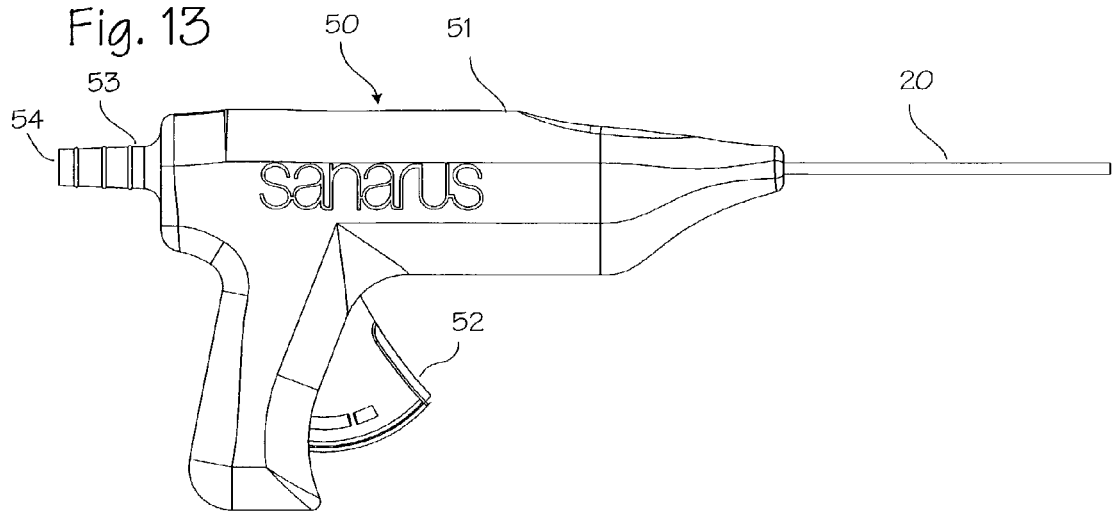
FIG. 13 illustrates a biopsy gun adapted for use with the adhesion probe of FIG. 1.

FIG. 13 shows a biopsy gun 50 for use with the adhesion probe of FIG. 1. The biopsy gun comprises a housing 51, the cannula 20, and a trigger 52 for driving the cannula distally. At the proximal end of the housing, a snap fitting 53 with an inlet 54 communicates with the lumen of the cannula. The cannula extends from within the housing at the inlet and out through the distal end of the housing. The cannula is adapted for insertion through a small incision in the skin.

Figure 14:
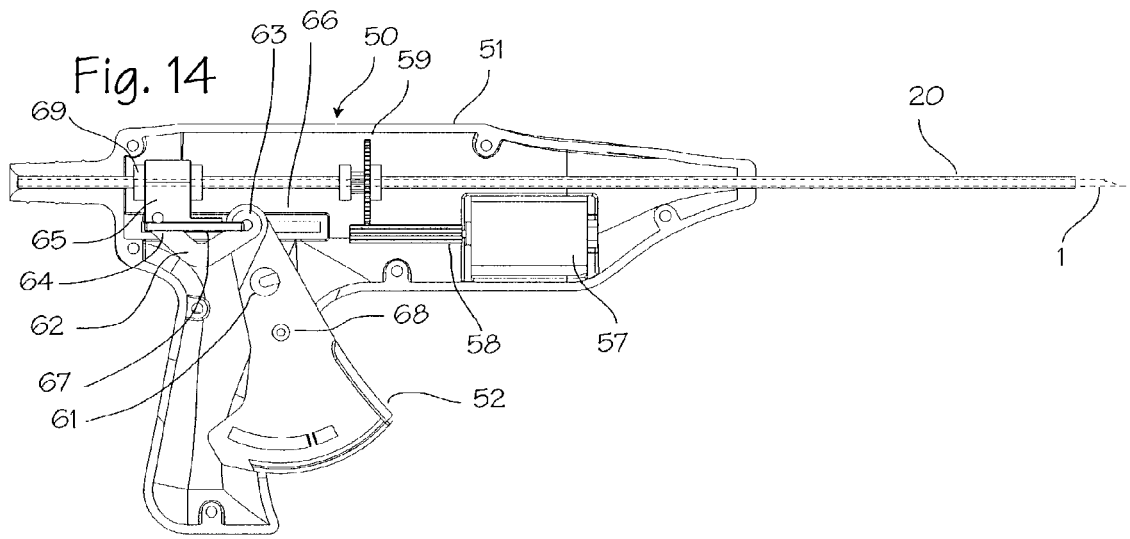
FIGS. 14 and 15 are cross sections of the biopsy gun of FIG. 13.
Figure 15:
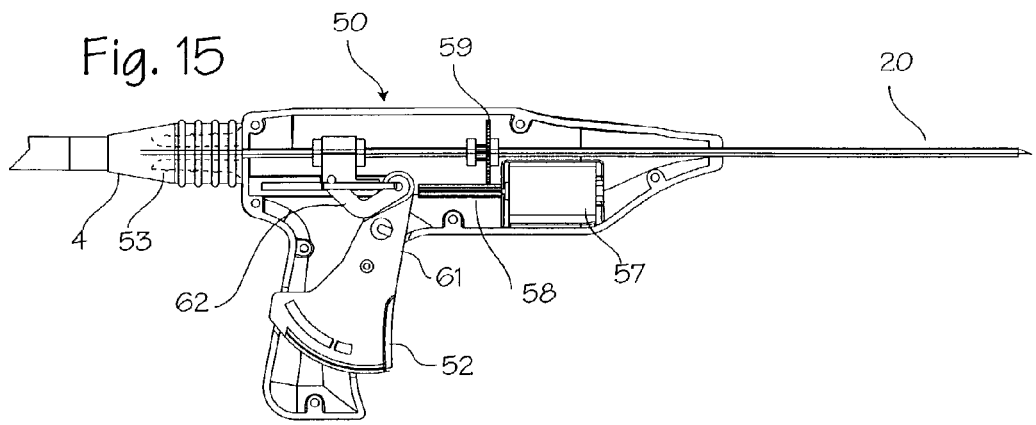

FIGS. 14 and 15 illustrate the biopsy gun in cross section. As shown in the cross sections, the biopsy gun 50 includes a coring mechanism that includes a cannula rotating mechanism and a cannula translating mechanism. The cannula rotating mechanism comprises a motor 57, a pinion gear 58, and a drive gear 59. The drive gear has a bore sized to fit the cannula 20. The cannula is rotationally fixed into the drive gear through the bore, so that rotation of the drive gear results in corresponding rotation of the cannula. The pinion gear is rotatably coupled to the motor at one end and its gear teeth mesh with the drive gear. When the motor is activated, the motor causes the pinion gear to rotate. The rotation of the pinion gear is translated to the drive gear to rotate the drive gear and thereby rotate the cannula. The rotating mechanism may be used during coring to assist in cutting a core sample from surrounding tissue.

The cannula translating mechanism comprises the trigger 52, trigger upper extension 61, a pivotable arm 62 with a first end 63 connected to the trigger and a second end 64 connected to a carriage 65. The carriage is slidably mounted in a track 66 via a rail 67 that fits into the track. The track is fixedly attached to the housing 51, or formed integrally into the housing, and is preferably duplicated on both sides of the housing. The rail is slidably mounted onto the track with the arm pivotably attached to the carriage at the proximal end of the carriage. The trigger is pivotably mounted to the housing about a pivot pin 68 and attached to the first end of the arm. The carriage is attached to the second end of the arm. The cannula 20 is loosely fitted through the carriage. The bearings 69 are fixed to the cannula on either side of the carriage, and allow the cannula to be rotatable within the carriage but longitudinally locked to the carriage, so that any longitudinal (proximal or distal) movement of the carriage causes corresponding longitudinal movement of the cannula.

The cannula translating mechanism has a proximal position and a distal position. FIG. 14 illustrates the translating mechanism in the proximal position, where the cannula will not be engaged with the tumor. In the proximal position, the carriage 65 is positioned at the proximal end of the track 66 and the penetrating segment 3 of the adhesion probe 1 is exposed, extending distally from the cannula. FIG. 15 illustrates the translating mechanism in the distal position, with the cannula translated distally over the penetrating segment of the adhesion probe, where it will engage and core a tumor secured to the penetrating segment. To move the translating mechanism to the distal position, the trigger 52 is depressed. As the trigger is depressed, the trigger rotates about the pivot pin 68 to advance the arm 62 and the rail 67 to the distal end of the track, thereby also advancing the carriage to the distal end of the track. As the carriage advances from the proximal end to the distal end of the track, the cannula 20 advances from the proximal end of the gun 50 to the distal end of the gun. Any tissue stuck to the tip of the adhesion probe when the cannula is advanced is cored from the surrounding lesion, and may be removed with the device.

FIG. 15 also shows the adhesion probe 1 in place within the lumen 23 of the cannula 20. The adhesion probe can be inserted into and through the lumen from the proximal opening 21 of the cannula. To secure the adhesion probe to the gun 50, the handle 4 of the adhesion probe is snap fitted to the snap fitting 53. The gas and/or liquid source is connected to the handle via the feed line.

Figure 16:
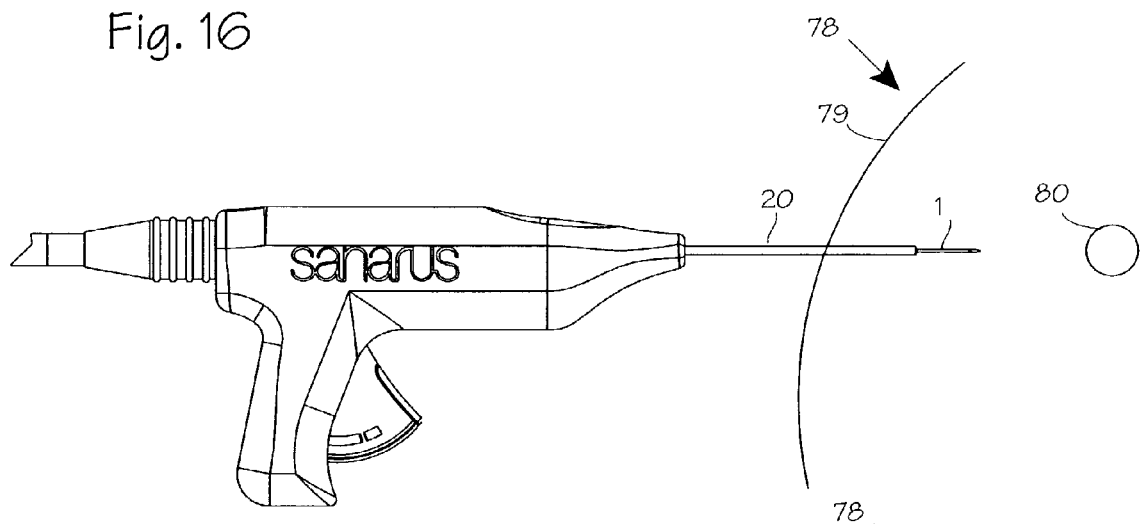
FIG. 16 illustrates a method of breast tumor biopsy using the device of FIG. 13.

FIGS. 16 through 19 illustrate the device in use. FIG. 16 shows the adhesion probe 1 and the cannula 20 being inserted through the incision made in the skin overlying the tumor. The patient's breast 78 and skin 79 are shown schematically. The tumor, lesion or other suspect mass 80 is located within the breast, surrounded by soft tissue and fatty tissue. An ultrasound scanner or other imaging device is used to obtain an image of the breast, including the tumor and any device inserted into the breast, and the surgeon uses the display from the imaging device to assist in guidance of the probe and the cannula to the tumor.

Figure 17:
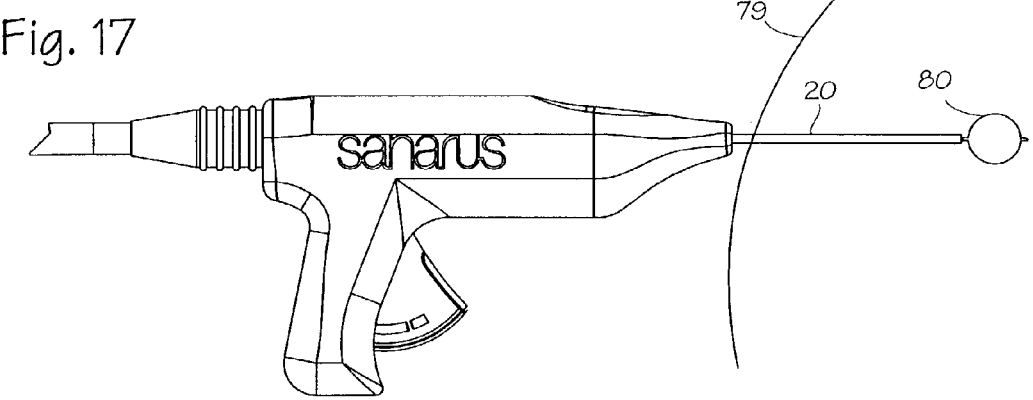
FIG. 17 illustrates a method of breast tumor biopsy using the device of FIG. 13.

FIG. 17 illustrates the adhesion probe 1 and the cannula 20 being inserted into the breast until the probe penetrates the tumor 80. The surgeon pushes the probe and the cannula into the breast until the penetrating segment 3 of the adhesion probe 1 pierces through the tumor and until the tapered segment 15 of the rigid tube 2 is proximate to the tumor.

Figure 18:
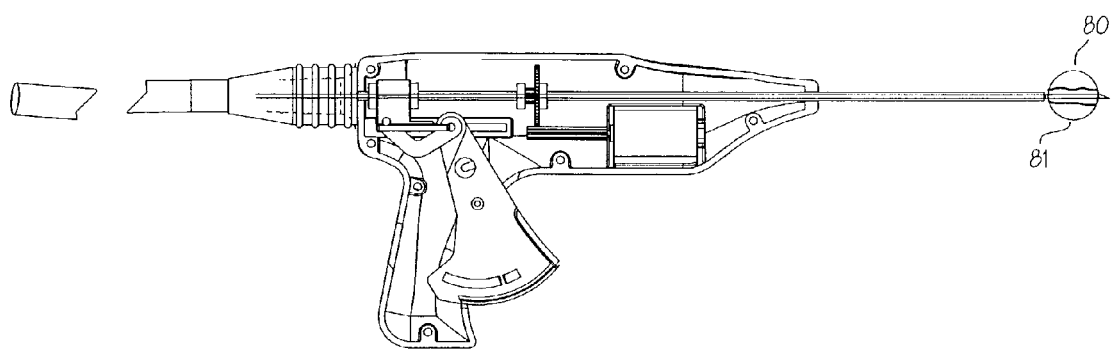
FIG. 18 illustrates a method of breast tumor biopsy using the device of FIG. 13.

FIG. 18 illustrates the adhesion probe 1 being activated to secure the tumor 80. To secure the tumor to the probe during the biopsy procedure, the surface area about the penetrating segment 3 is cooled. Either gas or liquid is directed from the source to the penetrating segment. If the surgeon uses gas, as the gas is directed out through the orifice 11 of the coolant inlet tube, the gas undergoes a Joule-Thomson effect to freeze the surface area about the penetrating segment. The cooled annular volume of body tissue is illustrated in FIG. 18 as item 81. The gas source can be a high compression tank or a whippet. The surface area is frozen to a temperature range of about 0° C. to −60° C. At this temperature range, the cooled surface area does not ablate the tumor cells to hinder tumor cell analysis. Only a relatively small amount of gas or liquid is needed to cool the surface area to this temperature range. The gas or liquid exiting the orifice and counterflowing along the annular cavity 16 is exhausted from the probe. The cooled surface area freezes a thin layer of tumor cells in contact about the cooled surface area, and the tumor is secured to the probe.

Figure 19:
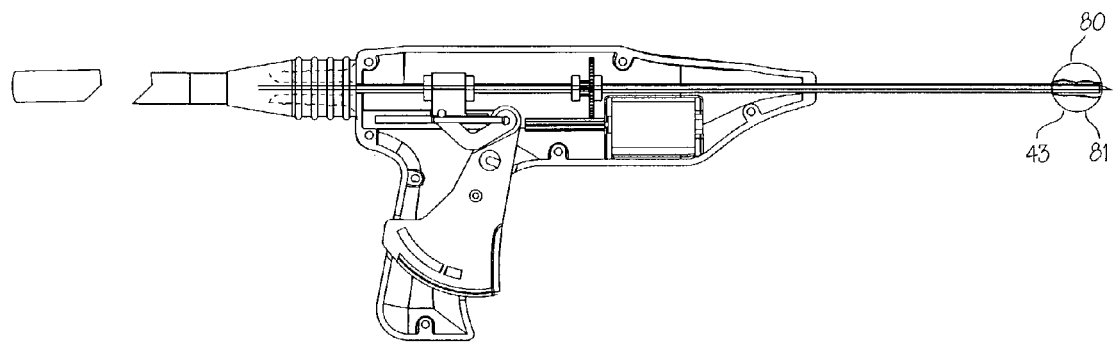
FIG. 19 illustrates a method of breast tumor biopsy using the device of FIG. 13.

FIG. 19 illustrates activation of the coring mechanisms to cut a core sample of the frozen tumor 80. Once the tumor is secured to the probe, the biopsy gun is activated to core a sample of the frozen tumor. The rotating mechanism of the gun may be activated while the translating mechanism is still in the proximal position. To begin coring the tumor, the translating mechanism is operated via the trigger. The trigger is depressed and the cannula advances distally towards the frozen tumor. As the cannula contacts the tumor and advances towards the sharp distal tip, the rotating cannula cuts a sample of the frozen tumor. The resulting core sample is a layer of frozen or partially frozen tumor tissue about the penetrating segment 3. Because the tumor is frozen, dispersion and seeding of the tumor cells to healthy areas of the breast is minimized compared to normal biopsy methods.

Once a sample of the breast tumor is cored, the coring mechanism is deactivated with the cannula remaining in the distal position. The adhesion probe 1 with the secured core sample remains within the cannula. To remove the core sample from the breast, the biopsy gun and the adhesion probe are retracted from the breast, with the core sample still protected within the cannula during retraction. Once the gun and probe are retracted outside the breast, the adhesion probe with the core sample 43 is withdrawn from the gun out from the inlet 10, or out the distal end of the cannula, as shown in FIG. 11. The sample is still secured to the distal segment of the adhesion probe 1, and can be removed as previously illustrated in FIG. 12.

Figure 20:
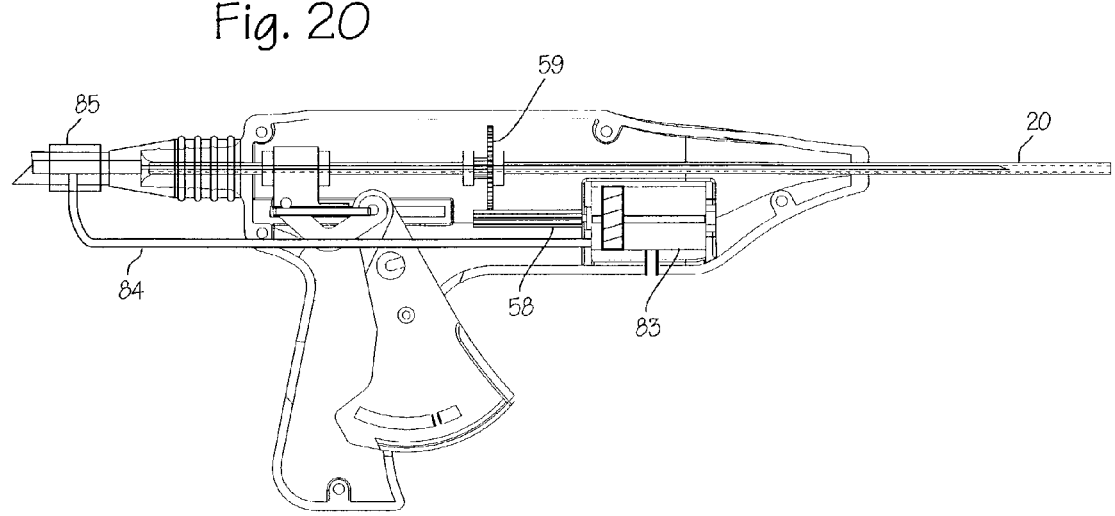
FIG. 20 is a cross section of a biopsy gun provided with a gas turbine motor and adapted for use with the adhesion probe of FIG. 1.
Figure 21:
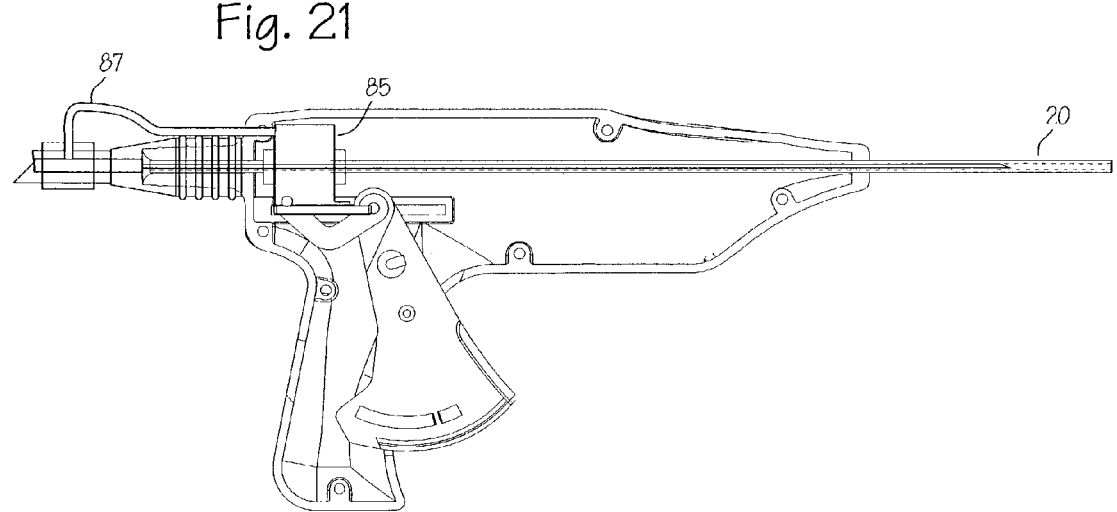
FIG. 21 is a cross section of a biopsy gun provided with a gas turbine motor and adapted for use with the adhesion probe of FIG. 1.

FIG. 20 illustrates an alternative coring mechanism, showing a gas turbine 83 in place of the motor of the previous figures. This turbine is powered by the exhaust gas from the adhesion probe, thereby eliminating the need for an electric motor. A flexible tube 84 is connected to the exhaust pathway of the adhesion probe or gas supply line through a coupling 85, and is also coupled to the turbine, directing exhaust gas into the turbine. A suitable turbine gas control valve 86 may be used to control gas supply to the turbine. The cannula 20 is rotatably coupled to the gas turbine using the same type of pinion gear and drive gear arrangement as is used for the electric motor. FIG. 21 illustrates another embodiment of the turbine driven coring mechanism, in which the turbine is mounted directly on the cannula, in the place of the carriage of the previous embodiments, and is slidably mounted within the housing. The tubing 87 is flexible, allowing distal and proximal translation of the turbine during operation. The turbine driven devices of FIGS. 20 and 21 may be used in the same manner as the biopsy instruments and guns of FIGS. 4 and 13.

The adhesion probe and methods of use described above have been developed for use with a cryosurgical system, which controls a relatively high volume coolant source, and can also be used to operate cryoprobes to cryoablate lesions, tumors and other target masses in the breast. The adhesion probe and biopsy apparatus (biopsy instrument and biopsy gun) are conveniently combined with such pre-existing cryosurgical system to take advantage of cooling sources already in place in an operating room. The adhesion probes and biopsy devices of FIGS. 22 and 23, however, are designed for stand-alone use, so that a physician does not need a cryosurgical system on site in order to take advantage of the method of cryo-adhesion. FIG. 22 illustrates a self-contained adhesion probe. The self-contained adhesion probe includes the rigid tube 2 with the penetrating segment 3. Inside the rigid tube, coolant inlet tube 10 with an orifice 11 extends to the first segment 13 of the penetrating segment. At the proximal end of the rigid tube, screw threads or other releasable fittings are provided to permit releasable attachment to the gas source. The rigid tube is fitted with a sharp distal tip 14. Exhaust gas is vented through vent 88 on the proximal segment of the rigid tube. The gas source is provided in the form of a canister 89 of compressed gas. Carbon dioxide ($CO_2$) is a suitable gas, and is readily available in the form of cylinders (whippet chargers, bulbs or capsules). Liquid freon and other refrigerants are also a suitable coolants which can be obtained in small canisters or spray cans. The canister is releasably mounted into a bracket or holder 90. The holder has a fitting 91 for receiving the proximal end of the rigid rod and providing secure releasable attachment. The holder as a second fitting 92 which matches the fittings on the proximal end of the biopsy apparatuses. The output 93 of the canister is directed to the inlet 94 of the coolant inlet tube 10 through the pass-through port in the holder.

As illustrated in FIG. 23, the rigid tube may be removed from the gas source and holder to provide a simple needle configuration. This assembly can be used in much the same was as the embodiments using a gas hose (FIGS. 7-10 and 16-19), but may also be used in an "over-the-wire" method. In this method, the rigid rod is manipulated to penetrate the patient's breast and force the penetrating segment into the lesion. The biopsy apparatus is then threaded over the rigid tube, leaving the proximal end of the rigid tube extending slightly from the proximal end of the biopsy apparatus. The coolant holder is then threaded or otherwise secured onto the proximal end of the rigid tube, and the proximal releasable fitting is fitted into the receiving fitting on the holder. The cooling and coring steps are then accomplished as described above. This method permits easier manipulation of the adhesion probe into the tumor, and also eliminates reliance on large cryosurgical systems.

FIG. 24 illustrates a pneumatically operated biopsy instrument 100 adapted for use with the adhesion probe 1 of FIG. 1. The biopsy instrument comprises a housing 101 sized and shaped to form a convenient handle, and also to house the components of the instrument. The various tubes used in the instrument are fitted through an inlet 102 at the proximal end 103 of the housing. The biopsy instrument further comprises the cannula 20 which extends from within the housing and out through the distal end 104 of the housing. As in the previous embodiments, the cannula is slidably fitted over the adhesion probe. The adhesion probe itself passes entirely through the housing in this embodiment.

As shown in FIG. 24, the biopsy instrument includes a coring mechanism which serves as both a translating mechanism and a rotating mechanism for the cannula. The combined translating/coring mechanism performs the rotating operation as it performs the longitudinal translation of the cannula that is required for coring. The cannula translating mechanism is comprised of a pneumatic or hydraulic actuator 105 which includes a cylinder or piston chamber 106, a proximal closure head 107 and a distal closure head 108, a piston 109, a fluid supply port 110 in the proximal closure head, and an actuator rod 111 which is threaded form of a lead screw or jack screw. The cylinder can be formed from the inner surface of the housing, or the housing may be integrally formed with the cylinder. The piston is disposed within the piston cylinder chamber, such that the piston, although tightly fitting within the cylinder chamber, is capable of translating longitudinally along the cylinder. It may also be rotatable relative to the cylinder operating fluid is supplied to (and drawn from) the actuator through actuator supply tube 112. The supply tube extends from the operating fluid source (not shown), through the inlet 102 of the housing, and to the cylinder fluid supply port, such that the distal end of the tube communicates with the cylinder. The supply tube and the adhesion probe pass through the inlet in side-by-side relationship.

The piston is attached to the cannula 20, and is longitudinally fixed to the cannula. The piston may be rotatably fixed to the cannula, but the cannula may also be longitudinally fixed to the piston while remaining freely rotatable relative to the piston. The piston has a bore with a diameter chosen to closely match the outer diameter of the cannula, so that the cannula is held tightly by piston within the bore. The cannula is longitudinally fixed into the bore of the piston, such that the translation of the piston distally and proximally through the cylinder is translated to the cannula. The cannula extends from the proximal end of the housing, through the piston bore, through the actuator rod 111, and out through the distal closure head. (Alternatively, the cannula can terminate proximally within the cylinder, so long as it is fixed to the piston chamber.) In the embodiment shown, the adhesion probe and cannula are coaxially disposed within the piston, actuator rod and cylinder.

The cannula rotating mechanism is comprised of a lead screw 111 (which also serves as the actuator rod) and a lead screw nut 113. The lead screw nut is disposed at the distal end of the piston cylinder 106, within the distal closure head (it may be formed integrally with the distal closure head). The lead screw is formed of a tube, with screw threads on the outside of the tube and a lumen passing through the tube. The proximal end of the lead screw is longitudinally fixed to the piston 109, such that the lumen of the lead screw communicates with the bore of the piston. (The cannula passes through the lumen of the lead screw.) The lead screw nut is adapted to receive the lead screw. The lead screw is screwed into and through the lead screw nut, such that the lead screw extends from within the piston cylinder 106 out through the lead screw nut to the exterior of the cylinder. The cannula 20 passes through the lumen of the lead screw and is rotationally fixed into the lead screw, either directly or indirectly. When the piston is translated, the lead screw translates under operation of the piston and rotates via translation through the lead screw nut. The lead screw can have a pitch of (1) inch per revolution, such that for every inch of translation, the lead screw rotates one revolution. Because the cannula is rotationally fixed to the cannula, the rotation of the lead screw is translated to the cannula.

The cannula translating mechanism has a retracted/proximal position and an extended/distal position. FIG. 24 illustrates the translating mechanism in the retracted position, where the cannula 20 will not be engaged with the tumor. In the retracted position, the piston is positioned at the proximal end of the cylinder and the penetrating segment of the adhesion probe 1 is exposed, extending distally from the cannula. FIG. 25 illustrates the translating mechanism in the extended position, with the cannula translated distally over the penetrating segment 3 of the adhesion probe, where it will engage and core a tumor secured to the penetrating segment. To move the translating mechanism from the retracted position to the extended position, a gas is supplied to the cylinder via the gas/vacuum tube 112. Based upon the configuration of the piston and cylinder, it is preferred that the gas pressure range be about 60 psi to 120 psi. However, other gas pressure ranges can be used depending on other piston-cylinder configurations. When there is sufficient gas pressure within the cylinder, the piston translates distally to the distal end of the cylinder. Under operation of the piston, the lead screw 111 and the cannula are translated distally. The cannula translates distally over the penetrating segment of the adhesion probe. As the cannula translates, the cannula rotates under operation of the lead screw and lead screw nut assembly. Any tissue stuck to the tip of the adhesion probe when the cannula is translated and rotated is cored from the surrounding lesion, and may be removed with the instrument, as described in the earlier figures. To move the translating mechanism back to the retracted position, a vacuum is provided to the cylinder via the gas/vacuum tube. Based upon the configuration of the piston and cylinder, the degree of vacuum necessary to draw the piston proximally may vary. Under the vacuum force, the piston translates proximally to the proximal end of the cylinder. Under operation of the cylinder, the lead screw and the cannula translate proximally, and rotate during translation as the lead screw is draw back through the lead screw nut. The single feed actuator described in these figures can be replaced with an equivalent dual feed actuator, where high pressure operating fluid is supplied to both sides of the piston to move the piston distally and proximally. However, the arrangement shown simplifies the construction of the cylinder minimizes then number of components that must be housed within the housing.

Figure 26:
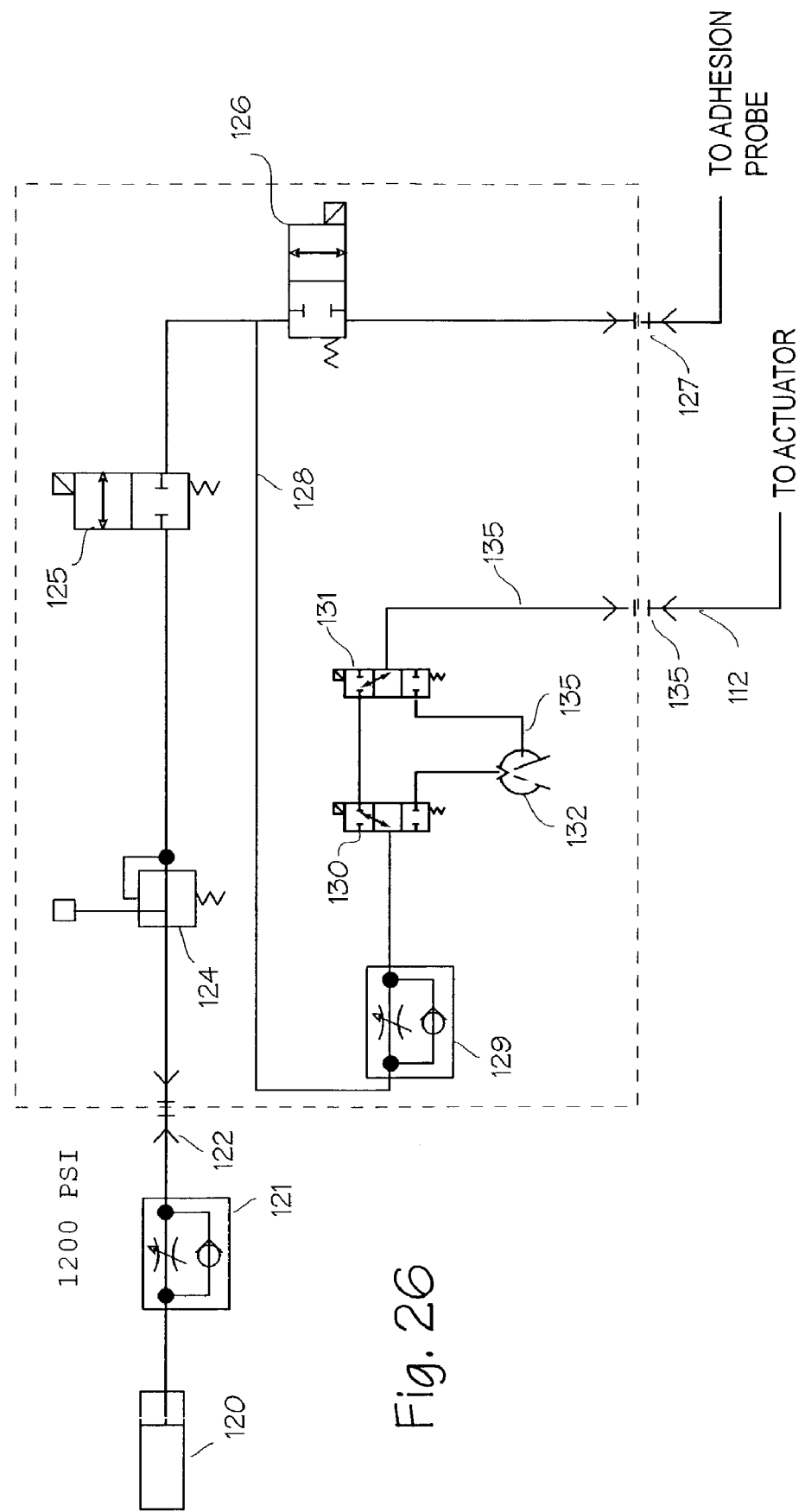
FIG. 26 is a schematic diagram of the pneumatic system for operating the biopsy instrument of FIGS. 24 and 25.

FIG. 26 is a schematic diagram of the pneumatic system for operating the biopsy instrument of FIGS. 24 and 25. The cooling gas is supplied from a tank 120 of cooling gas, such as argon or nitrogen stored at high pressure, through a high pressure supply line 121. External pressure regulator 122 regulates pressure in the line to desired pressure for high pressure supply to the manifold of valves shown through pressure fitting 123. The supply line inside the manifold is provided an internal pressure regulator 124 which regulates pressure in the line to desired pressure for high pressure supply to the adhesion probe (1000-3000 psi). A manifold supply valve 125 and an adhesion probe supply valve 126 are operable to control flow of high pressure gas to the adhesion probe. From the high pressure valve 126, the downstream portion of the high pressure supply line 121, designated as item 121d, connected to the adhesion probe through high pressure fitting 127. Control of the pneumatic cylinder it accomplished with lower pressure gas from tap line 128 through pneumatic gas pressure regulator 129, which is set to provide gas in the range of about 60-120 psi, though the pressure range may be varied depending on the system composition. The low pressure regulator supplies gas to a first three-way valve 130, which in turn selectively supplies low pressure gas to the second three way valve 131 or the operating fluid inlet 132 of jet Venturi pump 133 (also referred to as an ejector pump or an induction pump). The second three way valve selectively connects the actuator supply line 134 (which is connected to actuator supply tube 112 through pressure fitting 135) to operating gas provided from the first three way valve, or connects the actuator supply tube 112 to the vacuum inlet 136 of the jet Venturi pump. To supply low pressure gas to the actuator and force the coring cannula distally, the operator or control system operates the three way valves to connect the low pressure gas supply to actuator supply line 134, selectively operating the first three way valve to supply high pressure gas to the second three way valve, and operating the second three way valve to supply the high pressure gas to the actuator supply line. To apply a vacuum to the actuator and force the coring cannula to retract proximally, the operator or control system operates the first three way valve to supply low pressure gas to the operating fluid inlet of the jet Venturi pump and operates the second three way valve to connect the actuator supply line to the vacuum inlet of the Venturi pump. The control of the system may be accomplished with direct operator control of the various valves, or it may be accomplished through a computer system. For the jet Venturi pump, the JSM90 model vacuum pump supplied by Vaccon Co., Inc. provides suitable vacuum pressure to operate the actuator.

Various embodiments of coring means, translating means, and rotating means can be used in place of the spring operated translating means of FIGS. 4 through 6 or the translating means and rotating means of FIGS. 13 through 15 and FIGS. 24 and 25. The cannula can be fitted with a slide bolt, for example, which can then be manually pushed distally in the holders to advance the cannula. The cannula may merely be forced over the adhesion probe by hand, without the assistance of the coring mechanisms. The adhesion probe has been described in embodiments which use coolants to cool the probe and target tissue and thereby make the probe adhere to the target tissue. Alternatively, heating elements such as RF heating elements, resistive heating elements, ultrasound heating elements and the like may be used to heat the probe and target tissue and thereby make the probe adhere to the target tissue. In such embodiments, the heating should be limited to that necessary for light necrosis of the target tissue that does not penetrate deeply into the target tissue, or to a small longitudinal segment of the tissue, so that a viable biopsy core may be obtained. However, if the entire tumor or lesion is to be removed with the aid of the adhesion probe, heating need not be so limited.

The devices and methods illustrated above have been illustrated in relation to the treatment of tumors and lesions within the breast. However, they may be used to treat tumors and lesions throughout the body wherever the tumors which are difficult to secure and locate are encountered. Thus the devices and methods may be used for tumors and lesions of the uterine tube (such as uterine fibroids), kidney, liver, prostate or brain.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A system for securing a mass within the breast of a human patient, said system comprising:
    a rigid tube adapted for insertion into the body of the patient, said rigid tube having a proximal end, a distal end, a proximal segment, and a distal segment, said proximal segment having a larger outer diameter than the distal segment;
    said distal segment having a penetrating element adapted for piercing the mass;
    a gas supply tube for delivering a coolant to the distal end of the rigid tube, said gas supply tube being disposed within the rigid tube, extending to the distal end of the rigid tube and terminating in an orifice at the distal end of the rigid tube, thereby forming an annular lumen between the inner surface of the rigid tube and the outer surface of the gas supply tube, whereby the coolant gas may flow from the gas supply tube, through the annular lumen, and then be exhausted outside the body of the patient;
    said gas supply tube being sized relative to the rigid tube such that, when coolant is supplied to the rigid tube at a pressure within a predetermined pressure range, cooling of the distal end of the rigid tube is limited to the range of 0° C. to −60° C., whereby cells in the mass are adhered to the rigid tube without ablating the cells;
    a housing encasing the proximal end of the rigid tube and the gas supply tube, wherein the distal segment of the rigid tube is capable of extending into the body of the patient; and
    a canister of coolant gas operably attached to the gas supply tube, said canister also disposed within the housing.

2. The system of claim 1 further comprising a pressure regulator for regulating the pressure within the gas supply tube, whereby the pressure is kept within the predetermined pressure range.

3. The system of claim 1 further comprising a fitting disposed on the proximal end of the rigid tube, wherein the rigid tube may be removably attached to the housing.

4. The system of claim 3 further comprising a fitting disposed on the gas supply tube, wherein the canister may be removably attached to the gas supply tube.

5. The system of claim 1 wherein the mass has a predetermined approximate length, and the distal segment has a length approximately the same as the predetermined approximate length of the mass.

6. The biopsy device of claim 1 wherein the lumen of the cannula has an internal diameter, at the distal end of the cannula, substantially exceeding the outer diameter of the distal segment of the adhesion probe, thereby defining an annular space between the distal segment of the adhesion probe and the distal end of the cannula suitable for obtaining a sample of the mass when the cannula is disposed over the adhesion probe such that the distal segment of the adhesion probe is within the distal end of the cannula.

7. A biopsy device for securing and coring a mass within the breast of a human patient during a biopsy of said mass, said biopsy device comprising:
    an adhesion probe comprising:
        a rigid tube adapted for insertion into the body of the patient, said rigid tube having a proximal end, a distal end, a proximal segment having a first outer diameter, a distal segment having a second outer diameter, the first outer diameter being larger than the second outer diameter;
        said distal segment adapted to be adhered to the mass within the breast;
    a cannula, having a proximal end and a distal end, adapted for use with the adhesion probe, and said cannula comprising:
        a tube having a lumen extending from the proximal end to the distal end, said lumen having an internal diameter approximately matching the first outer diameter of the proximal segment of the adhesion probe;
        said cannula adapted for insertion into the body of the patient over the adhesion probe; and
        said cannula being slidable over the adhesion probe.

8. The biopsy device of claim 7 further comprising:
    a cannula rotating mechanism operably connected to the cannula to rotate the cannula relative to the device;
    a cannula translating mechanism operably connected to the cannula to move the cannula distally and proximally relative to the device; and
    a housing encasing the cannula, the rotating mechanism, and the translating mechanism, said housing having a proximal end and a distal end, the cannula extending from within the housing and out through the housing at the distal end of the housing.

9. The coring device of claim 8 wherein the cannula rotating mechanism comprises a motor, a pinion gear operably coupled to the motor, a drive gear rotatably coupled to the pinion gear, said drive gear having a bore sized to fixedly fit the cannula, the cannula being fitted through the bore, whereby the motor may be operated to rotate the cannula.

10. The coring device of claim 8 wherein the cannula translating mechanism comprises a track, a carriage slidably attached to the track through a rail slidably disposed within the track, an arm operably connected to the carriage, a trigger rotatably mounted about a hub and operably attached to the carriage such that operation of the trigger effects distal and proximal movement of the cannula.

11. A biopsy device for securing and coring a mass within the breast of a human patient during a biopsy of said mass, said biopsy device comprising:
  an adhesion probe comprising:
    a rigid tube adapted for insertion into the body of the patient, said rigid tube having a proximal end, a distal end, a proximal segment, and a distal segment, said proximal segment having a larger outer diameter than the distal segment;
    said distal segment having a sharp distal tip adapted for piercing the mass;
    a high pressure gas supply tube for delivering a coolant to the distal end of the rigid tube, said gas supply tube being disposed within the rigid tube, extending to the distal end of the rigid tube, and terminating in an orifice at the distal end of the rigid tube, thereby forming an annular lumen between the inner surface of the rigid tube and the outer surface of the gas supply tube for exhausting the coolant from the probe;
  a coring device having a proximal end and a distal end, said coring device adapted for use with the probe, said coring device comprising:
    a cannula adapted for insertion into the body of the patient, said cannula having a lumen extending through the cannula and defining a proximal opening and a distal opening in the cannula;
    a cannula rotating mechanism operably connected to the cannula;
    a cannula translating mechanism operably connected to the cannula;
    a housing encasing the cannula, the cannula rotating mechanism, and the cannula translating mechanism, said housing having a proximal end and a distal end, the cannula extending from within the housing and out through the housing at the distal end of the housing; and
    a snap fitting disposed at the proximal end of the housing for securing the adhesion probe to the coring device, said snap fitting having an inlet communicating with the lumen of the cannula;
  wherein the adhesion probe is fitted through the lumen from the proximal opening of the cannula;
  wherein the adhesion probe is secured to the snap fitting of the coring device; and
  wherein the cannula is slidable over the adhesion probe.

12. The biopsy device of claim 11 wherein the cannula rotating mechanism comprises a motor, a pinion gear operably coupled to the motor, a drive gear rotatably coupled to the pinion gear, said drive gear having a bore sized to fixedly fit the cannula, the cannula being fitted through the bore, wherein, in an activated position, the motor rotates the cannula by rotating the pinion gear and the drive gear.

13. The biopsy device of claim 11 wherein the cannula translating mechanism comprises a track, an into track slidably attached to the track, an arm fixedly mounted on the into track, a trigger rotatably mounted about a pivot pin and operably attached to the track, a carriage slidably attached to the track, the cannula rotatably and fixedly attached to the carriage, wherein, in a disengaged position, the carriage is positioned at the proximal end of the track and wherein, in an engaged position, the carriage advances to the distal end of the track by depression of the trigger about the pivot pin.

14. A biopsy instrument for securing and coring a mass within the breast of a human patient during a biopsy of said mass, said biopsy instrument comprising:
  an adhesion probe comprising:
    a rigid tube adapted for insertion into the body of the patient, said rigid tube having a proximal end, a distal end, a proximal segment, and a distal segment, said proximal segment having a larger outer diameter than the distal segment;
    said distal segment having a sharp distal tip adapted for piercing the mass;
    a high pressure gas supply tube for delivering a coolant to the distal end of the rigid tube, said gas supply tube being disposed within the rigid tube, extending to the distal end of the rigid tube, and terminating in an orifice at the distal end of the rigid tube, thereby forming an annular lumen between the inner surface of the rigid tube and the outer surface of the gas supply tube for exhausting the coolant from the probe;
  a coring instrument, having a proximal end and a distal end, adapted for use with the probe, said coring instrument comprising:
    a cannula adapted for insertion into the body of the patient, said cannula having a lumen extending through the cannula and defining a proximal opening and a distal opening in the cannula;
    a cannula translating mechanism operably connected to the cannula;
    a housing encasing the cannula and the cannula translating mechanism, said housing having a proximal end and a distal end, the cannula extending from within the housing and out through the housing at the distal end of the housing; and
    a fitting disposed at the proximal end of the housing for securing the adhesion probe to the coring device, said fitting having an inlet adapted for communicating with the lumen of the cannula;
  said adhesion probe fitted through the lumen from the proximal opening of the cannula;
  said adhesion probe secured to the fitting of the coring instrument.

15. The biopsy instrument of claim 14 wherein the cannula translating mechanism comprises a rail, a block slidably attached to the rail, a trigger capable of coupling to the block such that operation of the trigger effects distal and proximal movement of the cannula, and a spring disposed between the block and the trigger for urging the block and the cannula distally, wherein, in a locked position, the block is positioned at the proximal end of the rail and the spring is compressed and wherein, in an unlocked position, the block advances to the distal end of the rail by depression of the trigger.

16. A device for obtaining a tissue sample from the body of a patient, said device comprising:
  an adhesion probe adapted for insertion into the body, said adhesion probe being operable to adhere to tissue within the body;
  a cannula disposed about the adhesion probe, said cannula being slidable over the adhesion probe; and an actuator comprising a cylinder, a piston disposed within the cylinder, and an actuator rod, said piston being longitudinally movable within the cylinder in response to application of pressure or a vacuum to the cylinder, said actuator rod being longitudinally fixed to the piston, said piston and actuator rod being longitudinally fixed to the cannula;

wherein the actuator is operable to cause the cannula to slide longitudinally over the adhesion probe.

17. The device of claim 16 wherein the cannula is rotatable over the adhesion probe and wherein the actuator is operable to cause the cannula to rotate over the adhesion probe.

18. The device of claim 16 wherein the actuator comprises a pneumatic actuator.

19. The device of claim 16 wherein the actuator comprises a hydraulic actuator.

20. A biopsy instrument for securing and coring a mass within the breast of a human patient during a biopsy of said mass, said biopsy instrument comprising:
   an adhesion probe comprising:
      a rigid tube adapted for insertion into the body of the patient, said rigid tube having a proximal end, a distal end, a proximal segment, and a distal segment, said proximal segment having a larger outer diameter than the distal segment;
      said distal segment having a sharp distal tip adapted for piercing the mass; and
      a high pressure gas supply tube for delivering a coolant to the distal end of the rigid tube, said gas supply tube being disposed within the rigid tube, extending to the distal end of the rigid tube, and terminating in an orifice at the distal end of the rigid tube, thereby forming an annular lumen between the inner surface of the rigid tube and the outer surface of the gas supply tube for exhausting the coolant from the probe;
   a coring mechanism, having a proximal end and a distal end, adapted for use with the probe, said coring mechanism comprising:
      a cannula adapted for insertion into the body of the patient, said cannula having a lumen extending through the cannula and defining a proximal opening and a distal opening in the cannula;
      a cannula translating mechanism operably connected to the cannula; and
      a cannula rotating mechanism operably connected to the cannula;
   a housing encasing the cannula, the cannula translating mechanism, and the cannula rotating mechanism, said housing having a proximal end and a distal end, the cannula extending from within said housing and out through the distal end of said housing;
   a fitting disposed at the proximal end of the housing, said fitting having an inlet adapted for communicating with the high pressure gas supply tube; and
   said adhesion probe fitted through the lumen of the cannula.

21. A method of securing a mass in the body of a patient, said method comprising;
   providing a system for securing a mass within the body of a patient, said system comprising:
      a rigid tube adapted for insertion into the body of the patient, said rigid tube having a proximal end, a distal end, a proximal segment, and a distal segment, said proximal segment having a larger outer diameter than the distal segment;
      said distal segment having a penetrating element adapted for piercing the mass;
      a coolant supply tube for delivering a coolant to the distal end of the rigid tube, said coolant supply tube being disposed within the rigid tube, extending to the distal end of the rigid tube, and terminating in an orifice at the distal end of the rigid tube, thereby forming an annular lumen between the inner surface of the rigid tube and the outer surface of the coolant supply tube, whereby the coolant may flow from the coolant supply tube, through the annular lumen, and then be exhausted outside the body of the patient;
      said coolant supply tube being sized relative to the rigid tube such that, when coolant gas is supplied to the rigid tube at a pressure within a predetermined pressure range, cooling of the distal end of the rigid tube is limited to the range of 0° C. to −60° C., whereby cells in the mass are adhered to the rigid tube without ablating the cells;
      a housing encasing the proximal end of the rigid tube and the gas supply tube, wherein the distal segment of the rigid tube is capable of extending into the body of the patient; and
      an inlet disposed in the housing and communicating with the coolant supply tube, wherein a source of coolant may be removably attached to the inlet;
   providing a coolant source;
   connecting said coolant source to the inlet;
   inserting the rigid tube into the body of the patient so that the distal segment of the rigid tube is disposed at least partially in the mass; and
   directing the coolant from the coolant source to the inlet to cool the distal segment of the rigid tube and to cool the mass immediately surrounding the distal segment of the rigid tube.

22. The method of claim 21 wherein the step of providing a coolant source comprises providing a source of high-pressure gas selected from the group consisting of argon, carbon dioxide and air.

23. The method of claim 21 wherein the step of providing a coolant source comprises providing a source of liquid nitrogen.

24. The method of claim 21 wherein step of providing a coolant source comprises providing a whippet of coolant gas.

25. The method of claim 21 wherein the step of providing the adhesion probe further comprises providing an adhesion probe structured such that the surface area about the distal segment of the rigid tubing and the rigid rod is cooled to a temperature range of about 0° C. to 60° C.

26. The method of claim 21 wherein the method of securing a mass comprises a method of securing a breast tumor within the breast of a patient.

27. The method of claim 21 further comprising the steps of:
   after the cooling the mass immediately surrounding the distal segment of the rigid tube, sliding a cutting cannula over the rigid tube to obtain a sample of mass surrounding the distal segment of the rigid tube.

* * * * *